(12) United States Patent
Russo

(10) Patent No.: US 12,257,045 B2
(45) Date of Patent: Mar. 25, 2025

(54) TRACKING INSERTION AND REMOVAL TIMES OF A CONTINUOUS GLUCOSE MONITORING SENSOR

(71) Applicant: Ascensia Diabetes Care Holdings AG, Basel (CH)

(72) Inventor: Anthony P. Russo, New York, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 110 days.

(21) Appl. No.: 17/374,897

(22) Filed: Jul. 13, 2021

(65) Prior Publication Data

US 2022/0015671 A1  Jan. 20, 2022

Related U.S. Application Data

(60) Provisional application No. 63/051,853, filed on Jul. 14, 2020.

(51) Int. Cl.
*A61B 5/145* (2006.01)
*A61B 5/00* (2006.01)

(52) U.S. Cl.
CPC ........ *A61B 5/14532* (2013.01); *A61B 5/0015* (2013.01); *A61B 5/14503* (2013.01); *A61B 5/6848* (2013.01)

(58) Field of Classification Search
CPC .............. A61B 5/14532; A61B 5/0015; A61B 5/14503; A61B 5/6848
See application file for complete search history.

(56) References Cited

U.S. PATENT DOCUMENTS 8,301,395 B2 * 10/2012 Matievich, Jr. .. G01N 35/00663
600/347
2007/0255122 A1 11/2007 Vol et al.
(Continued)

FOREIGN PATENT DOCUMENTS

CN    104602591 A    5/2015
CN    107438398      12/2017
(Continued)

OTHER PUBLICATIONS

U.S. Appl. No. 17/374,887, filed Jul. 13, 2021, Russo.
(Continued)

*Primary Examiner* — Jay B Shah
*Assistant Examiner* — Grace L Rozanski
(74) *Attorney, Agent, or Firm* — Erise IP, P.A.

(57) ABSTRACT

In response to insertion of a continuous glucose monitoring (CGM) sensor into the skin of user, a CGM system compares an identifier of the sensor to any previously-stored identifiers of previously-inserted sensors. If the identifier does not match a previously-stored identifier, indicating a newly-inserted sensor, the identifier and a time stamp are stored and CGM may begin. Upon removal of the sensor, a removal time stamp is stored. If the identifier of an inserted sensor matches a previously-stored identifier, indicating a reinserted sensor, a reinsertion time is obtained and an elapsed removal time is checked to determine whether it exceeds a maximum removal time limit. If it does, CGM is halted. If it does not, CGM may continue with the reinserted sensor. Methods of tracking insertion and removal times of a CGM sensor are also provided, as are other aspects.

24 Claims, 6 Drawing Sheets

(56) References Cited

U.S. PATENT DOCUMENTS

| | | | |
|---|---|---|---|
| 2010/0262380 A1 | 10/2010 | Matievich, Jr. et al. | |
| 2013/0245981 A1* | 9/2013 | Estes .................... | A61B 5/7203 |
| | | | 702/87 |
| 2014/0379358 A1 | 12/2014 | Chovanda et al. | |
| 2017/0367627 A1* | 12/2017 | Brister ................. | A61B 5/1468 |
| 2018/0182491 A1* | 6/2018 | Belliveau ............. | A61B 5/0004 |
| 2019/0190913 A1* | 6/2019 | Love .................... | A61B 5/1451 |
| 2019/0223765 A1 | 7/2019 | Harley-Trochimczyk et al. | |
| 2019/0239784 A1* | 8/2019 | Chavan .............. | A61B 5/14546 |

FOREIGN PATENT DOCUMENTS

| | | |
|---|---|---|
| EP | 1972269 A1 | 9/2008 |
| EP | 3243434 A1 | 11/2017 |
| JP | 2008506468 A | 3/2008 |
| JP | 2009078173 A | 4/2009 |
| TW | 201733519 A | 10/2017 |
| TW | 201944430 | 11/2019 |
| TW | 202002580 | 1/2020 |
| WO | WO2015100109 A1 | 7/2015 |
| WO | WO2017069867 A1 | 4/2017 |

OTHER PUBLICATIONS

International Search Report of International Application No. PCT/EP2021/069308 mailed Oct. 8, 2021.

Taiwan Patent Application 110125797, First Office Action, issued Oct. 9, 2024.

Japanese Patent Application 2023-501795, Office Action, issued Jan. 21, 2025.

* cited by examiner

500A

| ID | INSERTION TIME STAMP | MAX TIME | ELAPSED TIME | REMOVAL TIME STAMP | REINSERT TIME STAMP |
|---|---|---|---|---|---|
| 1234567 | 06:19:08:32 | 14:00:00 | 00:00:00 | 00:00:00:00 | 00:00:00:00 |
| 8765432 | 06:09:08:45 | 10:00:00 | 09:23:30 | 06:19:08:15 | 00:00:00:00 |
| 4321876 | 05:25:08:15 | 14:00:00 | 14:00:00 | 00:00:00:00 | 00:00:00:00 |
| ⋮ | ⋮ | ⋮ | ⋮ | ⋮ | ⋮ |

| ID | INSERTION TIME STAMP | MAX TIME | ELAPSED TIME | REMOVAL TIME STAMP | REINSERT TIME STAMP |
|---|---|---|---|---|---|
| 1234567 | 06:19:08:32 | 14:00:00 | 05:14:30 | 00:00:00:00 | 00:00:00:00 |
| 8765432 | 06:09:08:45 | 10:00:00 | 09:23:30 | 06:19:08:15 | 00:00:00:00 |
| 4321876 | 05:25:08:15 | 14:00:00 | 14:00:00 | 00:00:00:00 | 00:00:00:00 |
| ⋮ | ⋮ | ⋮ | ⋮ | ⋮ | ⋮ |

| ID | INSERTION TIME STAMP | MAX TIME | ELAPSED TIME | REMOVAL TIME STAMP | REINSERT TIME STAMP |
|---|---|---|---|---|---|
| 1234567 | 06:19:08:32 | 14:00:00 | 07:09:15 | 06:26:17:47 | 00:00:00:00 |
| 8765432 | 06:09:08:45 | 10:00:00 | 09:23:30 | 06:19:08:15 | 00:00:00:00 |
| 4321876 | 05:25:08:15 | 14:00:00 | 14:00:00 | 00:00:00:00 | 00:00:00:00 |
| ⋮ | ⋮ | ⋮ | ⋮ | ⋮ | ⋮ |

| ID | INSERTION TIME STAMP | MAX TIME | ELAPSED TIME | REMOVAL TIME STAMP | REINSERT TIME STAMP |
|---|---|---|---|---|---|
| 1234567 | 06:19:08:32 | 14:00:00 | 07:09:15 | 06:26:17:47 | 06:26:18:04 |
| 8765432 | 06:09:08:45 | 10:00:00 | 09:23:30 | 06:19:08:15 | 00:00:00:00 |
| 4321876 | 05:25:08:15 | 14:00:00 | 14:00:00 | 00:00:00:00 | 00:00:00:00 |
| ⋮ | ⋮ | ⋮ | ⋮ | ⋮ | ⋮ |

*FIG. 5D*

TRACKING INSERTION AND REMOVAL TIMES OF A CONTINUOUS GLUCOSE MONITORING SENSOR

CROSS REFERENCE TO RELATED APPLICATION

This claims the benefit of U.S. Provisional Patent Application No. 63/051,853, filed Jul. 14, 2020, the disclosure of which is hereby incorporated by reference herein in its entirety for all purposes.

FIELD

The invention relates generally to continuous glucose monitoring (CGM).

BACKGROUND

CGM has become a routine monitoring operation in diabetes care. By providing real-time glucose readings, therapeutic actions may be applied in a more timely fashion and a glycemic condition may be better controlled. During a CGM operation, a sensor of a CGM device is typically inserted subcutaneously and is continuously operated in an environment surrounded by tissue and interstitial fluid. The sensor inserted under the skin of a user provides a signal to a wireless transmitter unit of the CGM device that is indicative of the user's glucose level. Glucose readings may be performed automatically many times throughout the day (e.g., every few minutes or at some other pre-established time interval).

The CGM device may adhere to the outer surface of a user's skin, such as on the abdomen or the back of the upper arm, while the sensor is inserted through the skin to contact interstitial fluid. The sensor interacts with the interstitial fluid, generating electrical signals that are proportional to the amount of glucose present. These electrical signals are communicated to the transmitter unit for use in glucose level determinations.

The CGM device may be worn on the body for several days or even several weeks before removal and replacement of the sensor is required. Sometimes, a sensor may need to be removed and reinserted, e.g., to attend to a problem with adherence of the CGM device to the user's skin.

SUMMARY

In some embodiments, a continuous glucose monitoring (CGM) system is provided that includes a sensor unit having a sensor unit memory and a sensor, wherein the sensor unit memory has an identifier stored therein. The CGM system also includes a second memory configured to store therein a plurality of sensor identifiers. The CGM system further includes a real-time clock and a processor, wherein the processor is in communication with the second memory, the real-time clock, and the sensor unit. The processor is configured to execute computer instructions to (1) read the identifier stored in the sensor unit memory; (2) determine whether the identifier matches any previously-stored identifier in the second memory; (3) store the identifier and an insertion time stamp in the second memory in response to the identifier not matching any previously-stored identifier in the second memory, wherein the real-time clock is used to generate the insertion time stamp; (4) obtain a reinsertion time using the real-time clock in response to the identifier matching a previously-stored identifier in the second memory; and (5) determine whether the sensor has exceeded a predetermined maximum removal time limit using the reinsertion time.

In some embodiments, a continuous glucose monitoring (CGM) system is provided that includes a sensor configured to be inserted into skin of a user and to generate electrical signals indicative of a glucose level. The CGM system also includes a real-time clock, a first memory having an identifier stored therein identifying the sensor, a second memory configured to store therein a plurality of sensor identifiers, and a processor in communication with the real-time clock and the first and second memories. The processor is configured to execute computer instructions to (1) read the identifier stored in the first memory; (2) determine whether the identifier matches any previously-stored identifier in the second memory; (3) store the identifier and an insertion time stamp in the second memory in response to the identifier not matching any previously-stored identifier in the second memory, wherein the real-time clock is used to generate the insertion time stamp; (4) obtain a reinsertion time using the real-time clock in response to the identifier matching a previously-stored identifier in the second memory; and (5) determine whether the sensor has exceeded a predetermined maximum removal time limit using the reinsertion time.

In some embodiments, a method of tracking insertion and removal times of a continuous glucose monitoring (CGM) sensor is provided. The method includes reading an identifier of the sensor from a sensor unit memory via a processor executing computer instructions in response to activation of CGM; determining whether the identifier matches any previously-stored identifier in a second memory; storing the identifier and an insertion time stamp in the second memory in response to the identifier not matching any previously-stored identifier in the second memory; obtaining a reinsertion time in response to the identifier matching a previously-stored identifier in the second memory; determining whether the sensor has exceeded a predetermined maximum removal time limit using the reinsertion time; and stopping operation of the CGM in response to determining that the sensor has exceeded the predetermined maximum removal time limit.

Still other aspects, features, and advantages of this disclosure may be readily apparent from the following detailed description and illustration of a number of example embodiments and implementations, including the best mode contemplated for carrying out the invention. This disclosure may also be capable of other and different embodiments, and its several details may be modified in various respects, all without departing from the scope of the invention. For example, although the description below is related to continuous glucose monitoring, the devices, systems, and methods described below may be readily adapted to monitoring other analytes, such as, e.g., cholesterol, lactate, uric acid, alcohol, or the like, in other continuous analyte monitoring systems. This disclosure is intended to cover all modifications, equivalents, and alternatives falling within the scope of the appended claims (see further below).

BRIEF DESCRIPTION OF DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

FIGS. 5A, 5B, 5C, and 5D each illustrate a table stored in a memory listing CGM sensor identifiers, various time stamps, maximum insertion time limits, and elapsed insertion times according to embodiments provided herein.

DETAILED DESCRIPTION

Figure 1:
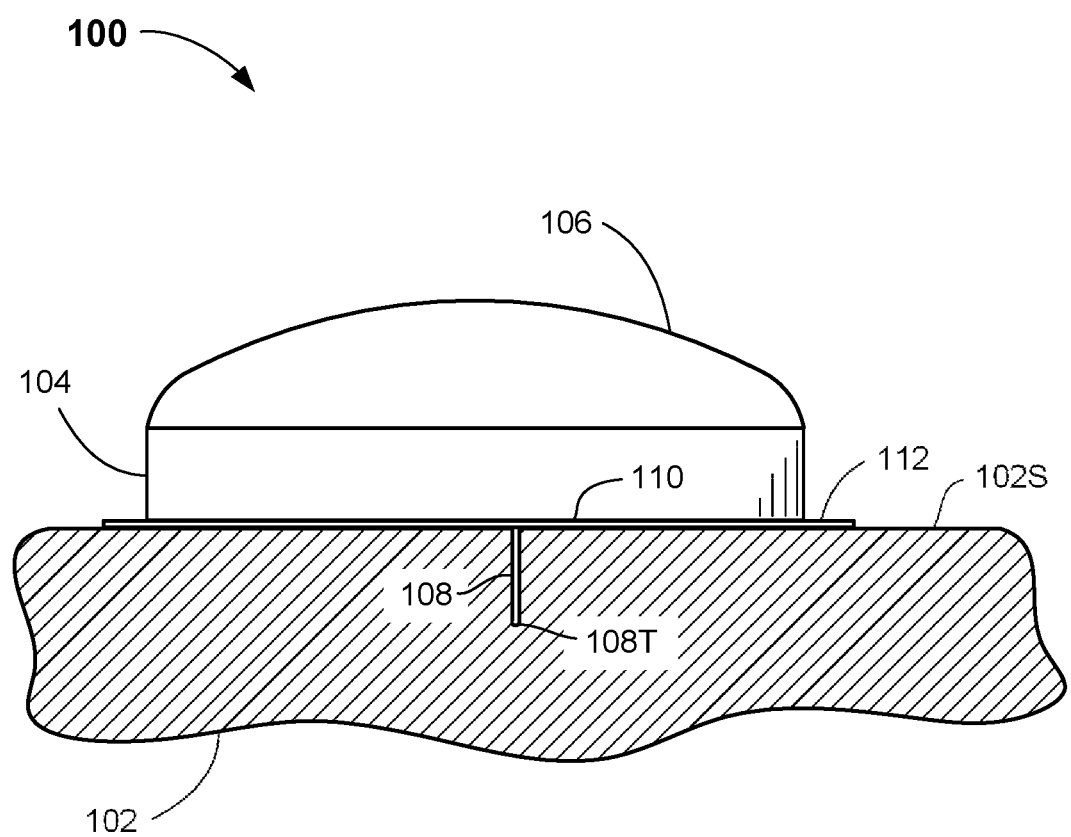
FIG. 1 illustrates a side elevation view of a continuous glucose monitoring (CGM) device that includes a sensor unit and a transmitter unit according to embodiments provided herein.

In order to more closely monitor and detect changes in a person's glucose concentration level, methods and systems for continuous glucose monitoring (CGM) have been developed. CGM methods and systems typically generate electrochemical glucose signals continuously during operation and perform glucose measurements/estimations based on the generated signals typically every few minutes.

CGM systems generally have a wearable portion (a CGM device) that is worn on the body and communicates (e.g., wirelessly) with an external device, such as a hand-held CGM receiver or other portable device, such as a smart phone executing a suitable application software program. The CGM device may be worn for several days or even one or two weeks before removal and replacement are required. The CGM device includes a sensor that is inserted (implanted) subcutaneously. The CGM device may also include analog circuitry coupled to the sensor and configured to bias the sensor and measure current signals generated by the inserted sensor, which is in contact with interstitial fluid. The CGM device may also include processing circuitry for determining glucose concentration levels based on measured current signals. The CGM device may further include electronic transmitter circuitry for communicating the determined glucose levels to an external device (e.g., a smart device or CGM receiver). The CGM device may be attached via, e.g., an adhesive, to the outer surface of the skin, such as to the abdomen, the back of the upper arm, or other suitable location.

CGM systems may provide frequent measurements of a user's glucose level without the need for each such measurement to be accompanied by the drawing of a blood sample, such as by finger sticks. CGM systems may still employ an occasional finger stick and the use of a blood glucose measuring (BGM) system, such as the Contour NEXT One® by Ascensia Diabetes Care AG of Basel, Switzerland, for initiating calibration of the CGM system.

The CGM device of a CGM system may generally be worn for up to about two weeks, after which the sensor may be removed and replaced. In some embodiments, the entire CGM device may be removed and replaced. In other embodiments, the CGM device may include a replaceable sensor unit that may be detached by the user from a reusable transmitter unit of the CGM device. In such embodiments, only the sensor unit of the CGM device may need to be removed and replaced.

A CGM system may be configured to notify a user via, e.g., a display message and/or audible alert when a sensor has reached its maximum allowable insertion time limit (e.g., 10 or 14 days) and should be replaced. A CGM system may also prevent glucose measurements from occurring with such an EOL ("end-of-life") sensor. A user, however, may attempt to reuse an EOL sensor by removing the sensor from the user's skin surface and then reinserting it into the skin as if it were new. For numerous health and performance reasons, a CGM system configured to prevent this from occurring would be desirable. A user may also, however, have an issue with a CGM device during operation, such as, e.g., a problem with the CGM device adhering to the user's skin surface, wherein the user may have to remove and reinsert the sensor to correct the problem. It would also be desirable for a CGM system to be configured to distinguish this situation from the attempt to reuse an EOL sensor. It would further be desirable for a CGM system to be configured to determine and prevent a reinserted sensor from being used if the reinserted sensor had been removed from the user's skin surface for too long a period of time. Such a sensor would no longer be sterilized and may possibly become contaminated, which may lead to health and/or other issues if reused.

In accordance with one or more embodiments, devices, systems, and methods of tracking insertion and removal times of a CGM sensor and subsequent detection of exceeding a maximum removal time limit and/or a maximum insertion time limit are provided herein, as will be explained in greater detail below in connection with FIGS. 1-5D.

FIG. 1 illustrates a wearable CGM device 100 inserted in skin 102 of a user according to one or more embodiments. CGM device 100 is configured to continuously monitor and provide periodic glucose readings (e.g., every 5 minutes or other suitable time interval). Although CGM device 100 is shown as partially dome shaped, CGM device 100 may have other shapes. CGM device 100 may include a sensor unit 104 and a transmitter unit 106. In some embodiments, sensor unit 104 and transmitter unit 106 may be integrally formed. In other embodiments, sensor unit 104 may be disposable, replaceable, and detachable from transmitter unit 106, which may be reusable with other sensor units. Sensor unit 104 and transmitter unit 106 may physically connect together via any suitable mechanical mechanism. When physically connected, sensor unit 104 and transmitter unit 106 may also be electrically coupled together so that data and control signals may be communicated and transmitted between electrical components in sensor unit 104 and transmitter unit 106. In some embodiments, initiation of communication between sensor unit 104 and transmitter unit 106 may be in response to physically connecting the two units together. In other embodiments, communication may be initiated by a command, such as a start command or the like. Communication between sensor unit 104 and transmitter unit 106 may be initiated in other suitable ways.

Sensor unit 104 may include a sensor 108, a portion of which is shown inserted through the user's skin 102. Sensor 108 may extend from sensor unit 104 through a baseplate 110 and may be configured to be at least partially located in interstitial fluid in a subcutaneous region of a user. Sensor 108 may be or may include an analyte sensor or an analyte sensor portion, such as at or near a sensor tip 108T. Sensor 108 may be inserted with an insertion device (not shown) having a sharpened needle or "introducer" that pierces the skin to introduce sensor 108 into a subcutaneous region of a user. Any suitable inserter device may be used.

Sensor unit 104 may also include an adhesive layer 112, which may be, e.g., a double-sided tape or pressure sensitive adhesive. One side of adhesive layer 112 may adhere to baseplate 110, while the other side of adhesive layer 112 may adhere to skin surface 102S of the user.

Transmitter unit 106 may include one or more electronic components that communicate with one or more electronic components within sensor unit 104 and with one or more external devices, as described in more detail below.

Figure 2:
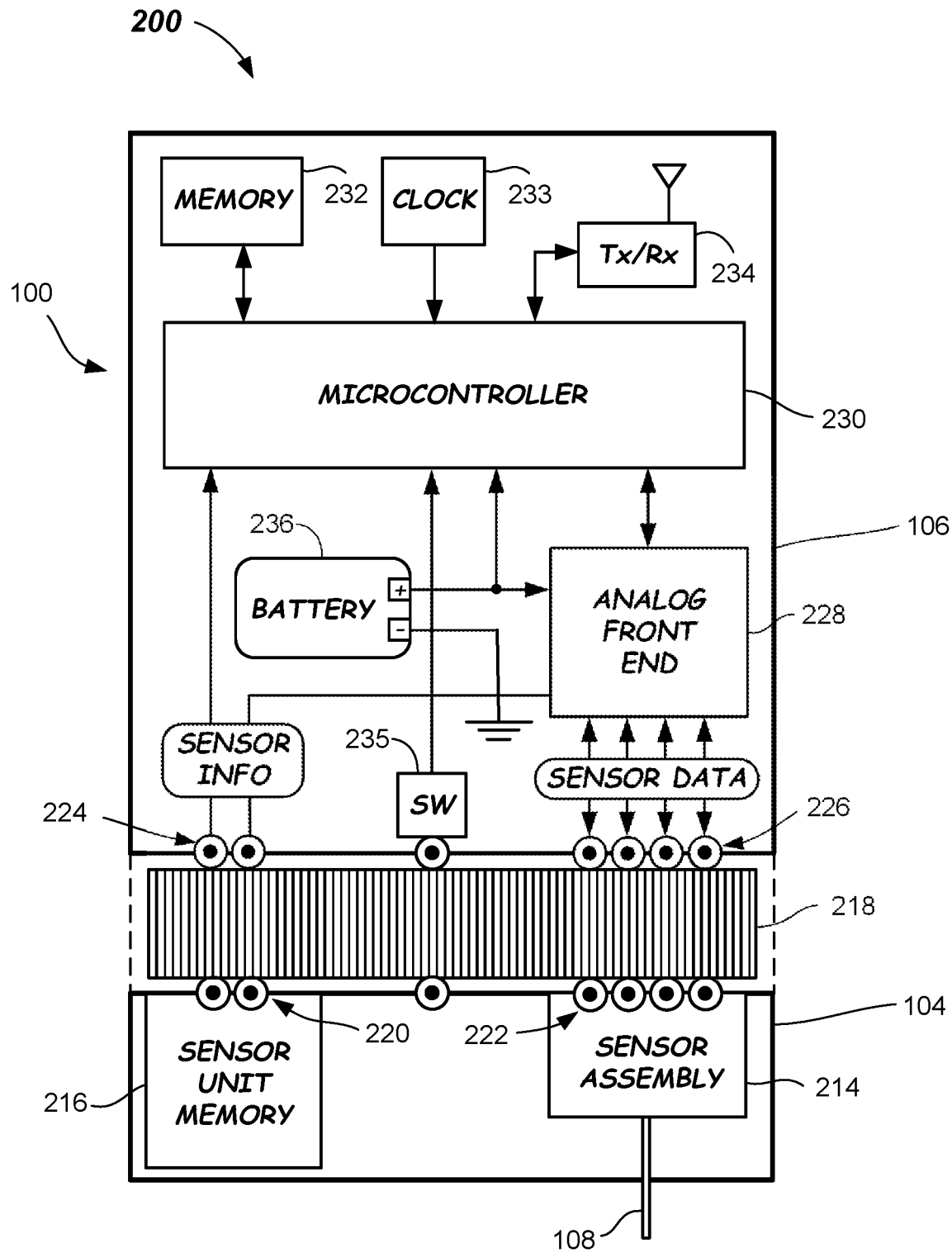
FIG. 2 illustrates a block diagram of the CGM device of FIG. 1 according to embodiments provided herein.

FIG. 2 illustrates a circuit component configuration 200 of CGM device 100 according to one or more embodiments. Sensor unit 104 may include a sensor assembly 214 and a sensor unit memory 216. Sensor assembly 214 may include sensor 108 and sensor circuitry (not separately shown) coupled to sensor 108. The sensor circuitry may apply at least one bias voltage to the analyte sensor portion of sensor 108, which may generate electrical signals while sensor 108 is in contact with the interstitial fluid. The sensor circuitry may also facilitate conducting electrical signals to and from sensor tip 108T of sensor 108 and/or other portions of sensor 108.

Sensor unit memory 216 may include a programmable read-only memory (PROM), an electrically erasable programmable read-only memory (EEPROM), a write once, read many memory (WORM), a static random access memory (SRAM), synchronous dynamic random-access memory (SDRAM), a physically unclonable function (PUF) (which may serve as a unique identifier), and/or NOR and NAND flash memories. Other suitable types of sensor memory circuitry may be used for sensor unit memory 216.

In some embodiments, sensor unit memory 216 may include a radiation hardened memory (rad-hard memory) or may be located within a rad-hard package that retains information (e.g., data) stored therein when the package and/or memory is exposed to radiation used to sterilize sensor unit 104.

Sensor unit memory 216 may store sensor information specific to that individual sensor unit and to components therein. For example, the sensor information may include a sensor unit identifier (e.g., a serial number of the sensor unit), a corresponding maximum insertion time limit (e.g., 3, 10, or 14 days), and a corresponding maximum removal time limit (e.g., 15, 45, or 60 minutes). The identifier may be unique or at least partially unique (e.g., a manufacturer may not reuse the same identifier within a certain period of time or certain geographical region such that a user inserting a sensor with an identifier identical to a different recently-inserted sensor is highly unlikely). The maximum insertion time limit is the period of time after which the sensor should be removed and replaced (i.e., the sensor has reached its EOL). The maximum removal time limit is a period of time after which a sensor that has been removed from a user's skin is deemed unsuitable (e.g., for health or performance reasons) for reinsertion and thus should not be reinserted even if the maximum insertion time limit had not been reached.

In some embodiments, the sensor information may also include, e.g., one or more of the following parameters:
 a) electrode sensitivity slope;
 b) manufacturing date;
 c) an expiration (shelf-life) date;
 d) batch or lot number;
 e) security code; and/or
 f) memory device version.

Other parameters and/or sensor information may be stored in sensor unit memory 216. Additionally or alternatively, some or all of the above parameters and/or sensor information may be encoded in a barcode or the like attached to sensor unit 104, CGM device 100, and/or packaging thereof.

In some embodiments, electrical data and control signals and power may be transmitted between sensor unit 104 and transmitter unit 106 via a connector 218, electrical contact pads 220 and 222 of sensor unit 104, and electrical contact pads 224 and 226 of transmitter unit 106 when sensor unit 104 and transmitter unit 106 are physically connected together.

Transmitter unit 106 may include an analog front end 228, a microcontroller 230 (or other similar processing resource), a memory 232, a real-time clock 233, a wireless transmitter 234, a switch 235, and a power source such as a battery 236. In some embodiments, transmitter unit 106 may include a local display (not shown) for displaying information such as glucose concentration information, sensor EOL, etc., without use of an external device.

Analog front end 228 may be configured to drive sensor assembly 214 and/or process sensor data generated by sensor assembly 214 and sensor 108. For example, analog front end 228 may be configured to apply a bias voltage to sensor assembly 214 and to measure resulting current flow through sensor assembly 214. Analog front end 228 in conjunction with sensor assembly 214 may apply the bias voltage to inserted sensor 108 located in interstitial fluid and may measure the resulting current, which is proportional to the glucose concentration. Analog front end 228 may perform other, fewer, or more functions.

Microcontroller 230 may be coupled to analog front end 228, memory 232, real-time clock 233, wireless transmitter 234, switch 235, and battery 236, and possibly other circuitry (not shown). Microcontroller 230 may include a processor such as, e.g., a microprocessor or other suitable processing circuitry, for processing sensor data generated by sensor assembly 214 and/or analog front end 228 and for detecting sensor reinsertion as described herein. Microcontroller 230 may also include, e.g., analog-to-digital converters for converting, e.g., analog current signals generated by sensor assembly 214 into digital current signals. Microcontroller 230 may further store digital current signal values in memory 232 and/or calculate or estimate glucose concentration levels based at least in part on the digital current signals. Microcontroller 230 may still further detect whether a sensor of a CGM device has met its maximum insertion time limit and/or whether a sensor of a CGM device has been reinserted and whether the reinserted sensor has exceeded its maximum removal time limit, as described in more detail below in connection with FIGS. 4-5D. Microcontroller 230 may perform other suitable functions.

Microcontroller 230 and/or other circuitry within transmitter unit 106 may be configured to electrically couple to and communicate with sensor unit memory 216. Microcontroller 230 may receive data stored in sensor unit memory 216 including, e.g., the identifier and maximum insertion and removal time limits of sensor unit 104, along with other of the above-described sensor information related to one or more parameters of one or more components of sensor unit 104. In some embodiments, a signal (e.g., a pull signal) may be transmitted from microcontroller 230 to sensor unit memory 216 to cause sensor unit memory 216 to transmit the data without user input. Thus, sensor unit memory 216 may automatically transmit the data to microcontroller 230 in response to connection of sensor unit 104 to transmitter unit 106. Alternatively, the transmission of sensor information from sensor unit memory 216 to microcontroller 230 may occur by way of a prompt, such as from the external device, or in any other suitable manner.

Microcontroller 230 may store the information received from sensor unit memory 216 in memory 232 and may use the information when calculating analyte concentrations, detecting whether sensor 108 has been reinserted (and if so, whether sensor 108 has met and/or exceeded maximum insertion and removal time limits), and performing other functions. In other embodiments, the information may remain in sensor unit memory 216 and may be accessed during CGM processing as needed by microcontroller 230 or other circuitry.

Additionally or alternatively, microcontroller 230 and memory 232 may receive sensor information from one or more barcodes or the like attached to sensor unit 104, CGM device 100, and/or packaging thereof via scanning by an external device in communication with transmitter unit 106.

Memory 232 may include computer program code stored therein that, when executed by the processor in microcontroller 230, causes CGM device 100 to perform various functions and/or to communicate with one or more external devices, such as a CGM receiver or a smart device (e.g., a smart phone or tablet) executing a CGM application software program that may calculate and/or display glucose levels and related data.

Memory 232 may also be configured to store a plurality of sensor unit identifiers corresponding to previously-used sensor units in those embodiments wherein sensor unit 104 is replaceable and detachable from transmitter unit 106, which is reusable with other sensor units. In some embodiments, identifiers corresponding to previously-used sensor units may be stored in, e.g., cloud-based storage and may be downloaded to memory 232 as needed.

Memory 232 may further include computer program instructions stored therein that, when executed by the processor in microcontroller 230, causes CGM device 100 to, in part, determine whether the identifier stored in sensor unit memory 216 matches any previously-stored identifier in memory 232, and determine whether sensor 108 has exceeded a predetermined maximum removal time limit in response to determining that the identifier stored in sensor unit memory 216 matches a previously-stored identifier in memory 232.

In some embodiments, memory 232 may be a radiation hardened memory (rad-hard memory) or may be located within a rad-hard package, similar or identical to sensor unit memory 216. Memory 232 may be a non-volatile memory, and may include, but is not limited to, an electrically programmable read-only memory (EPROM), an electrically erasable programmable read-only memory (EEPROM), and/or a flash memory (e.g., a type of EEPROM in either of the NOR or NAND configurations). Other types of suitable memory may be used for memory 232, including reading data from an Internet storage location, which may be cloud based.

In some embodiments, switch 235 may be any suitable mechanical or electrical switch that indicates whether or not sensor unit 104 is physically and electrically connected to transmitter unit 106. That is, switch 235 may have one output to indicate that sensor unit 104 is physically and electrically connected to transmitter unit 106, and another output to indicate that sensor unit 104 is not physically and electrically connected to transmitter unit 106 (e.g., when sensor 108 has been removed from the user's skin).

Additionally or alternatively to switch 235, in other embodiments, computer program instructions stored in memory 232 or a CGM application software program executing on an external device may have an encoded "software switch" that monitors whether or not any electrical current is received from sensor 108. If no current is received (or measured), the software switch may indicate an error condition (e.g., that sensor 108 has been removed from the user's skin).

Battery 236 may be located in and provide power to transmitter unit 106. In some embodiments, battery 236 may be rechargeable. Upon connection of sensor unit 104 to transmitter unit 106, battery 236 may also provide power to sensor unit 104. Providing power to sensor unit 104 may, in some embodiments, initiate communication between sensor unit 104 and transmitter unit 106, initiate detection of sensor insertion, and/or initiate CGM processing. In some embodiments, power may be provided to sensor unit 104 via analog front end 228. In other embodiments, battery 236 may be located within sensor unit 104 instead of transmitter unit 106, and in still other embodiments, sensor unit 104 and transmitter unit 106 may each have their own battery. Examples of battery 236 include flexible lithium polymer batteries, coin cell batteries such as lithium manganese, silver oxide, and alkaline coin batteries (e.g., CR 2032, SR516, and LR60 type coin batteries), or the like. Other power source/battery types may be used.

In some embodiments, microcontroller 230 may transmit electrical signals, glucose concentration information, and/or other information to one or more external devices via wireless transmitter 234. In some embodiments, microcontroller 230 may receive electrical signals, instructions, data, and/or other information from one or more external devices via wireless transmitter 234.

Figure 3:
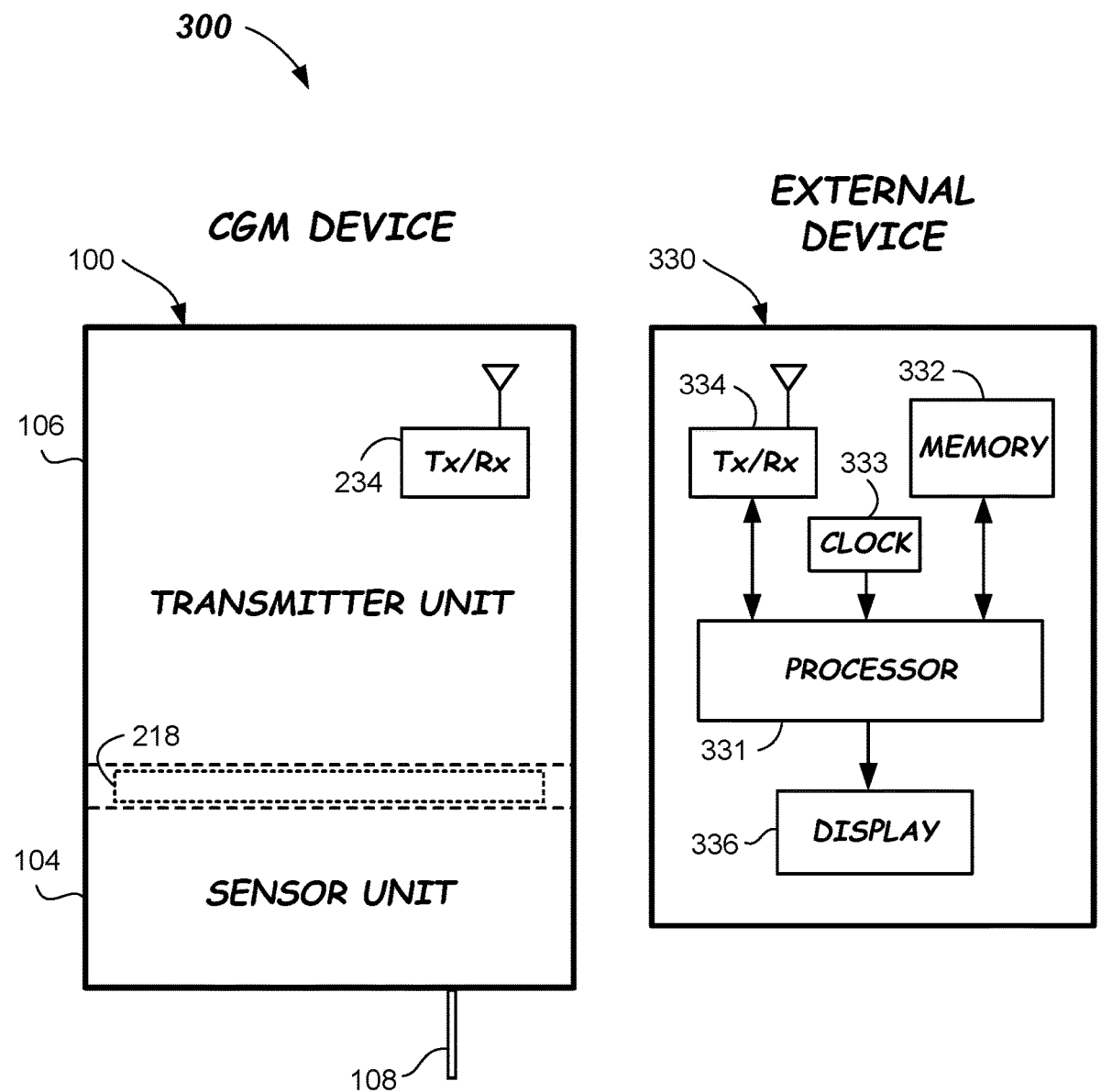
FIG. 3 illustrates a block diagram of a CGM system that includes a CGM device and an external device according to embodiments provided herein.

FIG. 3 illustrates a CGM system 300 according to one or more embodiments. CGM system 300 includes CGM device 100 and an external device 330. External device 330 may be, e.g., a dedicated CGM receiver or a smart device executing a CGM application software program. External device 330 may include a processor 331, a memory 332, a real-time clock 333, a wireless transmitter 334, and a display 336, wherein processor 331 is coupled to each of memory 332, real-time clock 333, wireless transmitter 334, and display 336, each of which may be any suitable device or component configured to perform at least some or all of the CGM related functions described herein. External device 330 may include other circuit components as well.

External device 330 and CGM device 100 may be communicatively coupled to each other via their respective wireless transmitters 234 and 334. Such wireless communication may occur via, e.g., any suitable standards-based communications protocols such as the Bluetooth® communications protocol. In some embodiments, wireless communication between external device 330 and CGM device 100 may occur via near-field communication (NFC), radio frequency (RF) communication, infra-red (IR) communication, optical communication, or any other suitable type of wireless communication. In some embodiments, external device 330 and CGM device 100 may additionally or alternatively communicate via one or more wired connections. In some embodiments, a security code matching a security code stored in sensor unit memory 216 may need to be input by the user into external device 330 before communication can be initiated between transmitter unit 106 and sensor unit 104 and/or between CGM device 100 and external device 330.

In some embodiments, at least some of the sensor information stored in sensor unit memory 216 of sensor unit 104 may be transferred to memory 332 of external device 330 via wireless transmitter 234 of CGM device 100 and wireless transmitter 334 of external device 330. The received sensor information may be processed by processor 331 and displayed on display 336. In some embodiments, some or all of the processing to determine glucose levels may be performed by processor 331, instead of by transmitter unit 106, and may be displayed on display 336. Other sensor information received by external device 330 may be displayed on display 336 to a user of CGM device 100. For example, the date of manufacture and/or an expiration date of sensor 108 and/or sensor unit 104 may be provided to the user, which may enable the user to determine whether sensor unit 104 and/or CGM 100 should be used.

In some embodiments, some or all of the processing to detect reinsertion of sensor 108 and to determine whether a reinserted sensor has exceeded its maximum removal time limit as described herein in connection with transmitter unit 106 may be performed by external device 330, instead of by transmitter unit 106. In particular, e.g., memory 332 of external device 330 may be configured to store a plurality of sensor unit identifiers corresponding to previously-used CGM devices (in those embodiments wherein sensor unit 104 and transmitter unit 106 are integrally formed) or previously-used sensor units (in those embodiments wherein sensor unit 104 is replaceable and detachable from transmitter unit 106, which is reusable with other sensor units). Also, in some embodiments, sensor information/data may be stored in cloud-based storage and retrieved therefrom to memory 332 by external device 330 as needed. In other embodiments, some or all sensor information/data may be encoded in one or more barcodes or the like attached to sensor unit 104, CGM device 100, and/or packaging thereof and retrieved therefrom to memory 332 by a scanner (not shown) of external device 330.

In those embodiments where sensor unit 104 and transmitter unit 106 are integrally formed, requiring CGM device 100 to be removed and replaced upon EOL of sensor 108, an identifier (e.g., serial number) of that CGM 100 may be stored in either sensor unit memory 216 or memory 232 of transmitter unit 106 and/or a barcode thereof. In some embodiments, a CGM device 100 having an integrally formed sensor unit 104 and transmitter unit 106 may have only a single memory (e.g., sensor unit memory 216 and memory 232 may be combined into a single memory device, which may still be referred to as a sensor unit memory), wherein the identifier may be stored. The CGM identifier may be transferred to memory 332 of external device 330 in response to insertion or reinsertion of CGM device 100 into the skin of a user.

Memory 332 of external device 330 may include computer program instructions, which may be part of a CGM application software program stored therein, that when executed by processor 331 causes processor 331 to, in part, determine whether the identifier stored in CGM device 100 matches any previously-stored identifier in memory 332, and determine whether sensor 108 has exceeded its predetermined maximum removal time limit in response to determining that the identifier stored in CGM device 100 matches a previously-stored identifier in memory 332.

Figure 4:
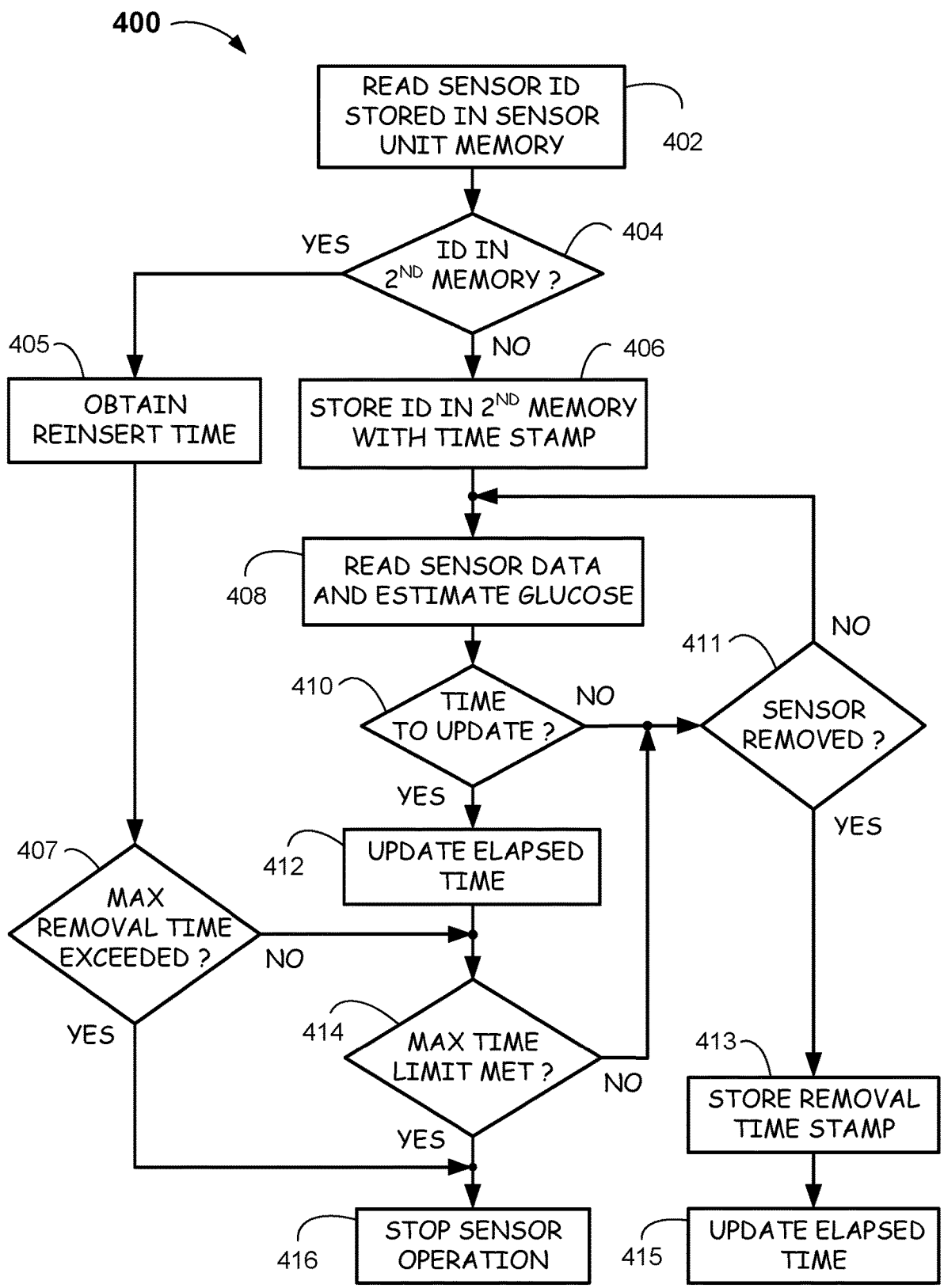
FIG. 4 illustrates a flowchart of a method of tracking insertion and removal times of a CGM sensor according to embodiments provided herein.

FIG. 4 illustrates a method 400 of tracking insertion and removal times of a sensor of a CGM device. In some embodiments, method 400 may also determine whether a reinserted sensor has exceeded a maximum removal time limit and should not be used. In still other embodiments, method 400 may determine whether a reinserted sensor has met its maximum insertion time limit and should be removed and replaced.

At process block 402, method 400 may begin by reading or receiving an identifier of an inserted sensor via a processor executing computer instructions in response to activation of CGM. Activation of CGM may occur in response to a power-up of the sensor unit, a user-entered command, or any other suitable manner of initiating CGM in response to insertion of a sensor into the skin of a user. The identifier may be, e.g., stored in a sensor unit memory of a sensor unit and/or encoded in a barcode attached to, e.g., the sensor unit, the CGM device, or packaging thereof. In some embodiments, the sensor may be sensor 108 of sensor unit 104 of CGM device 100, which may be part of CGM system 300 (see FIGS. 1-3). The sensor unit memory may be sensor unit memory 216 and the processor may be a processor of microcontroller 230 of CGM device 100 or processor 331 of external device 330, which is in communication with CGM device 100.

Method 400 may proceed to decision block 404 to determine whether the sensor identifier matches any identifier of a previously-inserted sensor that is stored in a second memory. The second memory may be, e.g., memory 232 located in transmitter unit 106 of CGM device 100 or memory 332 of external device 330. In some embodiments, the second memory may include a table as shown in each of FIGS. 5A-D.

FIGS. 5A, 5B, 5C, and 5D illustrate stored tables 500A, 500B, 500C, and 500D, respectively, each listing sensor identifiers ("IDs") and corresponding insertion time stamps, maximum allowable insertion times, elapsed insertion times, removal time stamps, and optional reinsertion time stamps of currently-inserted and/or previously-inserted sensors. Each of the insertion, removal, and optional reinsertion time stamps may have, e.g., a month:day:hour:minute format, which may be provided by a real-time clock such as, e.g., real-time clock 233 or 333 (of FIGS. 2 and 3, respectively). The maximum allowable insertion times and the elapsed insertion times may have, e.g., a days:hours:minutes format. Other suitable formats may be used for each entry. In some embodiments, an additional column for maximum allowable removal time limits may also be included.

Returning to decision block 404, if the determination is "NO," indicating that the sensor identifier is not in the second memory, the sensor is presumed to be new, and method 400 may proceed to process block 406.

At process block 406, the second memory is updated to include the new identifier, a corresponding insertion time stamp, and the sensor's maximum allowable insertion time (which may have been read or received from, e.g., the sensor unit memory or attached barcode). Entries for elapsed insertion time, removal time stamp, and optional reinsertion time stamp may each be zeroed. For example, referring to FIG. 5A, assume the newly-inserted sensor has an identifier of 1234567, which does not match any of the previously-stored identifiers. In response, the second memory is updated with sensor identifier 1234567, an insertion time stamp of 06:19:08:32 (month:day:hour:minute format, indicating the newly-inserted sensor was inserted on June 19 at 8:32 AM), and a maximum insertion time of 14:00:00 (days:hours:minutes format, indicating the maximum allowable insertion time for this sensor is 14 days). As shown in FIG. 5A, the most recent previously-inserted sensor had an identifier of 8765432 and the sensor before that had an identifier of 4321876.

Method 400 may proceed next to process block 408, where data from the sensor is read and a glucose level is determined/estimated based on the sensor data, as described above.

After each sensor reading and glucose level determination/estimation at process block 408 (which may occur at predetermined measurement intervals, such as, e.g., every 5 minutes), method 400 may proceed to decision block 410 to determine whether the elapsed insertion time of the currently-inserted sensor should be updated. The update may occur at any suitable time interval (e.g., every 5 minutes, every one or more hours, once per day, etc.), which preferably is an even multiple of the maximum insertion time limit.

If the determination is "YES" at decision block 410, indicating that elapsed insertion time of the sensor should be updated, method 400 may proceed to process bock 412, where elapsed insertion time for the currently-inserted sensor may be updated in a table stored in the second memory. Referring to FIG. 5B, e.g., the currently-inserted sensor 1234567 is shown as having an updated elapsed insertion time of 5 days, 14 hours, and 30 minutes in table 500B.

In alternative embodiments, instead of periodically updating an elapsed insertion time entry in a table stored in the second memory, process block 412 may periodically increment an elapsed insertion time counter while the sensor is inserted.

If the determination is "NO" at decision block 410, indicating that elapsed insertion time of the sensor does not need to be updated, method 400 may proceed to decision block 411, where continued insertion of the sensor is checked. That is, method 400 checks whether the sensor has been removed from the user's skin. Sensor removal may be detected via, e.g., switch 235 of transmitter unit 106 (see FIG. 2), which indicates whether or not sensor unit 104 is connected to transmitter unit 106. A disconnection may indicate that sensor unit 104 (and sensor 108) has been removed from the user's skin. Sensor removal may alternatively or additionally be detected via software when electrical signals from sensor 108 are no longer received by transmitter unit 106, which may indicate that sensor 108 is no longer in contact with a user's interstitial fluid.

If the determination is "NO" at decision block 411, indicating that the sensor has not been removed, method 400 returns to process block 408 to continue glucose monitoring. (A "YES" determination at decision block 411 is described further below.)

From process block 412, method 400 may proceed to decision block 414 to determine whether the sensor has met its maximum insertion time limit. A determination of "YES" at decision block 414 indicates that the sensor's elapsed insertion time, as indicated either in the table stored in the second memory or by the elapsed insertion time counter, equals the sensor's maximum insertion time limit. Note that in embodiments where the update interval is not an even multiple of the maximum insertion time limit, the elapsed insertion time may exceed the sensor's maximum insertion time limit. The elapsed insertion time equaling (or exceeding) the maximum insertion time limit at decision block 414 indicates the sensor has reached its EOL and should no longer be used. For example, referring to any of FIGS. 5A-D, assume that sensor 4321876 is the currently-inserted sensor. As shown, sensor 4321876 has a maximum insertion time of 14 days and an elapsed time of 14 days. Method 400 accordingly determines that sensor 4321876's maximum insertion time has been met and the sensor should no longer be used. Method 400 may then proceed to process block 416.

At process block 416, operation of the sensor is stopped. That is, a processor of CGM device 100 and/or external device 330 may signal the user with an error message or audible alert via an I/O device (e.g., a display and/or sound device) of CGM device 100 and/or external device 330 that glucose monitoring is halted and the sensor needs to be replaced. In some embodiments, CGM device 100 and/or external device 330 may prevent the sensor from operating and/or may prevent processing of any signals received from the sensor. Method 400 may end here until a sensor (new or previously-used) is inserted into the user's skin, which returns method 400 to process block 402.

Returning to decision block 414, a determination of "NO" indicates that the sensor has not met its maximum insertion time and is thus still usable. For example, referring to FIG. 5B, method 400 determines whether sensor 1234567's elapsed insertion time of 5 days, 14 hours, and 30 minutes equals (or exceeds) sensor 1234567's maximum insertion time limit of 14 days. Because it does not, method 400 may proceed to decision block 411, where continued insertion of the sensor is checked, as described above and below.

If the determination is "YES" at decision block 411, indicating that the sensor has been removed, method 400 may proceed to process block 413.

At process block 413, method 400 may store a removal time stamp in the second memory corresponding to the sensor that has just been removed. For example, referring to FIG. 5C, assume method 400 detects removal of sensor 1234567 at 5:47 PM on June 26. A removal time stamp of 06:26:17:47 may accordingly be stored in table 500C corresponding to sensor 1234567.

Method 400 may then proceed to process block 415, where the elapsed insertion time corresponding to the removed sensor is updated based on the removal time stamp. For example, again referring to FIG. 5C, the elapsed insertion time of sensor 1234567 is updated to 07:09:15 (7 days, 9 hours, and 15 minutes) based on the time difference between the removal time stamp (06:26:17:47) and the insertion time stamp (06:19:08:32).

In alternative embodiments wherein an elapsed insertion time counter is used as described above in connection with process block 412, method 400 at process block 415 may instead store in the second memory the value of the elapsed insertion time counter in response to detecting at decision block 411 that the sensor has been removed.

Method 400 may end at process block 415 until a sensor (new or previously-used) is inserted into the user's skin, wherein method 400 begins again at process block 402.

Returning to decision block 404, wherein method 400 determines whether an identifier of a sensor inserted into the user's skin matches any identifier of a previously-inserted sensor that is stored in the second memory, a "YES" determination indicates that the sensor identifier matches a previously-stored identifier in the second memory and, thus, the sensor is presumed to have been reinserted and is being reused. Method 400 may then proceed to process block 405.

At process block 405, method 400 may obtain a reinsertion time from a real-time clock, such as, e.g., one of real-time clocks 233 or 333, and may optionally store a reinsertion time stamp in the second memory corresponding to the reinserted sensor. For example, referring to FIG. 5D, assume sensor 1234567 had been removed (e.g., to adjust or replace an adhesive used to attach the sensor unit or CGM device to the user's skin surface) and has now been reinserted. A reinsertion time stamp of, e.g., 06:26:18:04, indicating that the sensor has been reinserted on June 26 at 6:04 PM, may optionally be stored in table 500D corresponding to sensor 1234567.

Method 400 may now proceed to decision block 407 to determine whether a maximum removal time limit of the sensor is exceeded. The maximum removal time limit may be stored in a memory of a sensor unit, transmitter unit, or cloud service, or encoded in a barcode, CGM application software program, or firmware of a CGM device. A maximum removal time limit may be established in accordance with safe medical practices regarding subcutaneous implantations and may range, e.g., from a few minutes to about an hour. Other maximum removal time limits may be possible. In some embodiments, tables 500A-D may include an additional column for storing a maximum removal time limit. To determine whether the maximum removal time limit of the sensor has been exceeded, method 400 determines an elapsed removal time by calculating the time difference between the reinsertion time (obtained directly from a real-time clock or from the reinsertion time stamp) and the removal time stamp. For example, referring to FIG. 5D, the time difference between the reinsertion time stamp of sensor 1234567 and the removal time stamp of sensor 1234567 is 17 minutes (06:26:18:04-06:26:17:47).

If the determination is "NO" at decision block 407, indicating that the sensor has not exceeded its maximum removal time limit and thus may be suitable for continued use, method 400 may proceed to decision block 414 to determine whether this previously-inserted sensor has met its maximum insertion time limit, as described above. This may prevent an EOL sensor from being reused.

Note that a reinserted sensor that has not met its maximum insertion time limit as determined at decision block 414 may continue to be used. In some embodiments, further updating of elapsed insertion time at process block 412 may continue to be based on the insertion time stamp or, in those embodiments in which an optional reinsertion time stamp is stored, may be based on that reinsertion time stamp.

If the determination is "YES" at decision block 407, indicating that the sensor has exceeded its maximum removal time limit and thus should not be used, method 400 may proceed to process block 416, where any continued use of this sensor is prevented, as described above.

In alternative embodiments, tables 500A-D may each include an error-detected column for indicating any error, defect, failure, or malfunction of a sensor, replaceable sensor unit, or replaceable CGM device detected during power-up or use thereof that would prohibit the continued use of that sensor, replaceable sensor unit, or replaceable CGM device, even though the sensor's maximum insertion time limit had not yet been met. In those alternative embodiments, an alternative decision block 414 may also determine whether any such error, defect, failure, or malfunction has occurred (as indicated in that error-detected column) in addition to determining whether the sensor's maximum insertion time limit has been met. In response to determining that such an error, defect, failure, or malfunction had occurred, or that the sensor's maximum insertion time limit had been met, alternative method 400 would proceed to process block 416 to stop operation of the sensor. In response to determining that no error, defect, failure, or malfunction had occurred, and that the sensor's maximum insertion time limit had not been met, alternative method 400 would proceed as described above.

Note that in some embodiments, tables 500A-D may store only a small number of identifiers (e.g., 5-10) corresponding to the most recently-used sensors. In some embodiments, tables 500A-D may be stored in memory 232 of transmitter unit 106, while in other embodiments, tables 500A-D may be stored in memory 332 of external device 330 or in a cloud-based memory.

Also note that some embodiments, or portions thereof, may be provided as a computer program product or software that may include a machine-readable medium having non-transient instructions stored thereon, which may be used to program a computer processor, system, controller, or other electronic device to perform a process or method described herein in accordance with one or more embodiments.

While the disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure or the claims.

What is claimed is:

1. A continuous glucose monitoring (CGM) system, comprising:
    a sensor unit, comprising:
        a sensor unit memory having an identifier stored therein; and
        an analyte sensor configured to be inserted into a subcutaneous region of a user for continuously monitoring a glucose concentration level of the user;
    an analog front end configured to apply a bias voltage to the analyte sensor and to measure a resultant current;
    a switch in communication with the sensor unit and configured to detect when the analyte sensor has been removed from a skin surface of the user;
    a second memory configured to store therein a plurality of sensor identifiers;
    a real-time clock; and
    at least one processor in communication with the second memory, the real-time clock, and the sensor unit, wherein the at least one processor is configured to execute computer instructions to:
        read the identifier stored in the sensor unit memory;
        determine whether the identifier matches any previously-stored identifier in the second memory;
        store the identifier and a skin insertion time stamp in the second memory in response to the identifier not matching any previously-stored identifier in the second memory, the real-time clock used to generate the skin insertion time stamp;
        receive, from the analog front end, the resultant current;
        determine the glucose concentration level based on the resultant current;
        in response to detecting, via the switch, the analyte sensor being removed from the skin surface, store a skin removal time stamp generated by the real-time clock in the second memory;
        in response to detecting, via the switch, the analyte sensor being reinserted into the skin surface and the identifier matching the identifier stored in the second memory, obtain a skin reinsertion time stamp of the analyte sensor using the real-time clock;
        determine an elapsed removal time of the analyte sensor based on the skin removal time stamp and the skin reinsertion time stamp;
        responsive to receiving an additional signal from the analyte sensor, determine whether the analyte sensor has exceeded a predetermined maximum removal time limit based on the elapsed removal time; and
        responsive to determining the analyte sensor has exceeded the predetermined maximum removal time limit, preventing continued use of the analyte sensor by preventing processing of any new signals from the analyte sensor.

2. The CGM system of claim 1, wherein an external device, a transmitter unit, or a cloud-based service comprises the second memory.

3. The CGM system of claim 1, wherein an external device or a transmitter unit comprises the at least one processor.

4. The CGM system of claim 1, further comprising a CGM device configured to be worn on the user, the CGM device comprising:
the sensor unit; and
a transmitter unit electrically connected to the sensor unit, the transmitter unit comprising a wireless transmitter, the real-time clock, and a microcontroller comprising the at least one processor.

5. The CGM system of claim 4, wherein the sensor unit and the transmitter unit are integrally formed.

6. The CGM system of claim 4,
wherein the sensor unit is replaceable and detachable from the transmitter unit, and
wherein the transmitter unit is reusable with other sensor units.

7. The CGM system of claim 1, wherein the at least one processor is further configured to execute computer instructions to read sensor data from the sensor unit and estimate a glucose level in response to:
storing the identifier and the skin insertion time stamp in the second memory; or
determining that the analyte sensor has not exceeded the predetermined maximum removal time limit and has not met a maximum insertion time limit.

8. The CGM system of claim 1, wherein the at least one processor is further configured to execute computer instructions to update periodically an elapsed insertion time of the analyte sensor using the real-time clock.

9. The CGM system of claim 8, wherein the at least one processor is further configured to execute computer instructions to determine whether the analyte sensor has met or exceeded a predetermined maximum insertion time limit in response to an updated elapsed insertion time.

10. A continuous glucose monitoring (CGM) system comprising:
a sensor unit, comprising:
an analyte sensor configured to be inserted into a subcutaneous region of a user for continuously monitoring a glucose concentration level of the user and to continuously generate electrical signals indicative of the glucose concentration level;
a first memory having an identifier stored therein identifying the analyte sensor;
an analog front end configured to apply a bias voltage to the analyte sensor to cause the generation of the electrical signals; and
a switch in communication with the sensor unit and configured to detect when the analyte sensor has been removed from a skin surface of the user;
a second memory configured to store therein a plurality of sensor identifiers;
a real-time clock; and
at least one processor in communication with the first memory, the second memory, and the real-time clock, wherein the at least one processor is configured to execute computer instructions to:
read the identifier stored in the first memory;
determine whether the identifier matches any previously-stored identifier in the second memory;
store the identifier and a skin insertion time stamp in the second memory in response to the identifier not matching any previously-stored identifier in the second memory, the real-time clock used to generate the skin insertion time stamp;
receive, from the analog front end, the electrical signals;
determine the glucose concentration level based on the electrical signals;
in response to detecting, via the switch, the analyte sensor being removed from the skin surface, store a skin removal time stamp generated by the real-time clock in the second memory;
detect when the analyte sensor was reinserted into the skin surface of the user using the switch;
in response to detecting, via the switch, the analyte sensor being reinserted into the skin surface and the identifier matching the identifier stored in the second memory, obtain a skin reinsertion time stamp of the analyte sensor using the real-time clock;
determine an elapsed removal time of the analyte sensor based on the skin removal time stamp and the skin reinsertion time stamp;
responsive to receiving an additional signal from the sensor, determine whether the analyte sensor has exceeded a predetermined maximum removal time limit based on the elapsed removal time; and
responsive to determining the analyte sensor has exceeded the predetermined maximum removal time limit, preventing continued use of the analyte sensor by preventing processing of any new signals from the analyte sensor.

11. The CGM system of claim 10, wherein a CGM device comprises the first memory, and an external device comprises the second memory, the real-time clock, and the at least one processor; or the first memory comprises a sensor unit memory of the sensor unit.

12. The CGM system of claim 10, wherein the first memory or the second memory is cloud based.

13. A method of tracking insertion and removal times of a continuous glucose monitoring (CGM) sensor, the method comprising: reading an identifier of an analyte sensor from a sensor unit memory of a sensor unit via at least one processor executing computer instructions, the analyte sensor configured to be inserted into a subcutaneous region of a user for continuously monitoring a glucose concentration level of the user, wherein the sensor unit is coupled to an analog front end configured to apply a bias voltage to the analyte sensor and to measure a resultant current; determining whether the identifier matches any previously-stored identifier in a second memory; storing the identifier and a skin insertion time stamp in the second memory in response to the identifier not matching any previously-stored identifier in the second memory; receiving, from the analog front end, the resultant current; determining the glucose concentration level based on the resultant current; in response to detecting, via a switch in communication with the sensor unit, the analyte sensor being removed from a skin surface, storing a skin removal time stamp in the second memory; in response to detecting, via the switch, the analyte sensor being reinserted into the skin surface and the identifier matching the identifier stored in the second memory, obtaining a skin reinsertion time stamp of the analyte sensor; determining an elapsed removal time of the analyte sensor based on the skin removal time stamp and the skin reinsertion time stamp; responsive to receiving an additional signal from the analyte sensor, determining whether the analyte sensor has exceeded a predetermined maximum removal time limit based on the skin removal time stamp and the skin reinsertion time stamp; and stopping operation of the CGM by preventing processing of any new signals from the analyte sensor in response to determining that the analyte sensor has exceeded the predetermined maximum removal time limit.

14. The method of claim 13 wherein the determining whether the analyte sensor has exceeded a predetermined maximum removal time limit comprises calculating an elapsed removal time of the analyte sensor based on the skin reinsertion time and a previously-stored removal time stamp.

15. The method of claim 13 further comprising reading sensor data via the analyte sensor and estimating a glucose level via the processor in response to: the storing the identifier and the skin insertion time stamp in the second memory; or determining that the analyte sensor has not exceeded the predetermined maximum removal time limit and has not met a maximum insertion time limit.

16. The method of claim 15 further comprising updating periodically an elapsed insertion time of the analyte sensor in response to the reading sensor data and the estimating the glucose level.

17. The method of claim 16 further comprising determining whether the analyte sensor has met or exceeded a predetermined maximum insertion time limit in response to the updating the elapsed insertion time.

18. The method of claim 17 further comprising stopping operation of the CGM and notifying the user that the analyte sensor has reached the predetermined maximum insertion time limit in response to determining that the analyte sensor has met or exceeded the predetermined maximum insertion time limit.

19. The method of claim 13, further comprising storing a skin removal time stamp in a third memory in response to detecting, via the switch, that the analyte sensor has been removed from the skin surface.

20. The method of claim 19 further comprising updating the elapsed insertion time of the analyte sensor in response to the storing the skin removal time stamp.

21. The CGM system of claim 1, wherein the switch is a software switch configured to monitor whether an electrical current is received from the sensor to determine when the analyte sensor is removed from the skin surface.

22. The CGM system of claim 3, wherein the at least one processor is further configured to execute computer instructions to transmit an error message or an audible alert to the external device in response to preventing processing of the analyte sensor.

23. The CGM system of claim 10, wherein the switch is a software switch configured to monitor whether an electrical current is received from the analyte sensor to determine when the analyte sensor is removed from the skin surface.

24. The CGM system of claim 1, wherein the at least one processor is further configured to execute instructions to:
responsive to detecting, via the switch, insertion of a new analyte sensor, compare a new analyte sensor identifier of the new analyte sensor to the any previously-stored identifier in the second memory;
responsive to determining the new analyte sensor identifier does not match the any previously-stored identifier in the second memory, determining a new glucose concentration level of the user based on a new resultant current obtained from the new analyte sensor.

* * * * *